United States Patent
Duffin

(10) Patent No.: US 6,230,059 B1
(45) Date of Patent: May 8, 2001

(54) IMPLANTABLE MONITOR

(75) Inventor: Edwin G. Duffin, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/271,107

(22) Filed: Mar. 17, 1999

(51) Int. Cl.$^7$ .................................................... A61N 1/37
(52) U.S. Cl. .......................................................... 607/60
(58) Field of Search ......................... 607/32, 60; 128/903; 600/300, 510

(56) References Cited

U.S. PATENT DOCUMENTS

| | | |
|---|---|---|
| 4,947,858 | 8/1990 | Smith . |
| 5,127,404 | 7/1992 | Wyborney et al. . |
| 5,305,761 * | 4/1994 | Byrne et al. ........................ 128/697 |
| 5,312,446 | 5/1994 | Holschbach et al. . |
| 5,313,953 | 5/1994 | Yomtov et al. . |
| 5,331,966 | 7/1994 | Bennett et al. . |
| 5,683,432 * | 11/1997 | Goedeke et al. ....................... 607/32 |
| 5,697,958 * | 12/1997 | Paul et al. ............................. 607/31 |
| 5,782,876 | 7/1998 | Flammang . |
| 5,851,221 | 12/1998 | Rieder et al. . |

FOREIGN PATENT DOCUMENTS 9802209    1/1998   (WO) .

* cited by examiner

Primary Examiner—William Kamm
(74) Attorney, Agent, or Firm—Reed A. Duthler; Harold R. Patton

(57) ABSTRACT

An implantable medical device (IMD) capable of monitoring physiologic data, distinguishing relatively noisy and noise free physiologic data, and recording noisy and relatively noise free segments of physiologic data in separate memory registers of a limited memory for retrieval and analysis at a later time. Preferably the physiologic data comprises the sampled EGM of the heart detected from sense electrode pairs that are implanted in the patient at sites where extraneous electrical noise, e.g., electromyographic signals, are also capable of being detected. The sense electrode pairs can constitute one or both sense electrodes located on or adjacent to the atrial and/or ventricular heart chambers and coupled to the IMD by a lead body or sense electrode pairs that are located remotely from the heart, e.g. at a subcutaneous implantation site of the IMD. A plurality of noisy EGM episode data registers store a corresponding plurality of noisy EGM episode data sets on a FIFO basis and another plurality of noise free EGM episode data registers to store a corresponding plurality of relatively noise free EGM episode data sets on a FIFO basis. Any form of discrimination of noisy data from relatively noise free data can be employed at the time of recording, but because the stored EGM episode data sets are subsequently viewed and analyzed by a physician, discrimination with absolute certainty is not required, and the physician can alter the detection criteria to fine tune it.

26 Claims, 7 Drawing Sheets

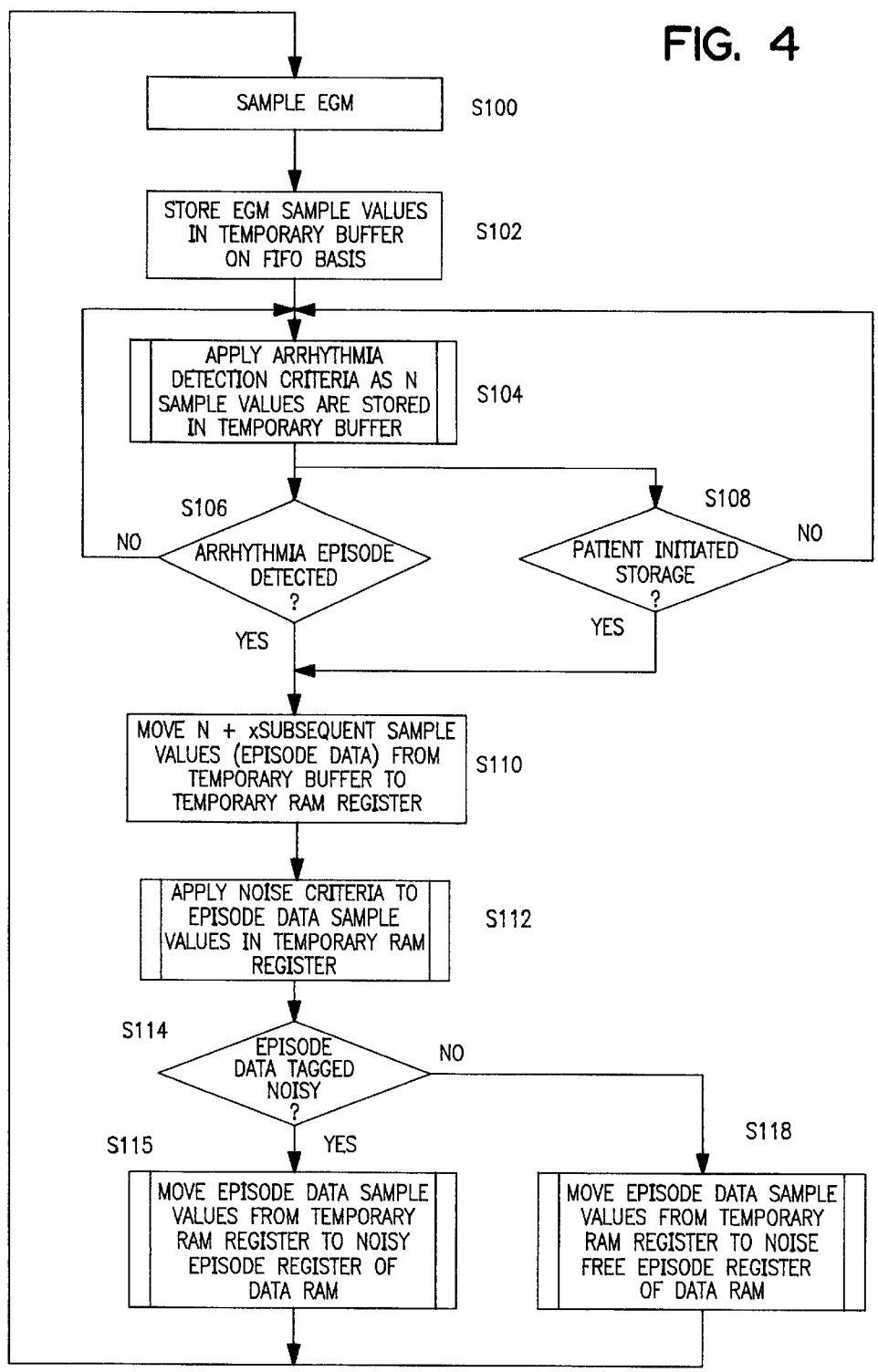

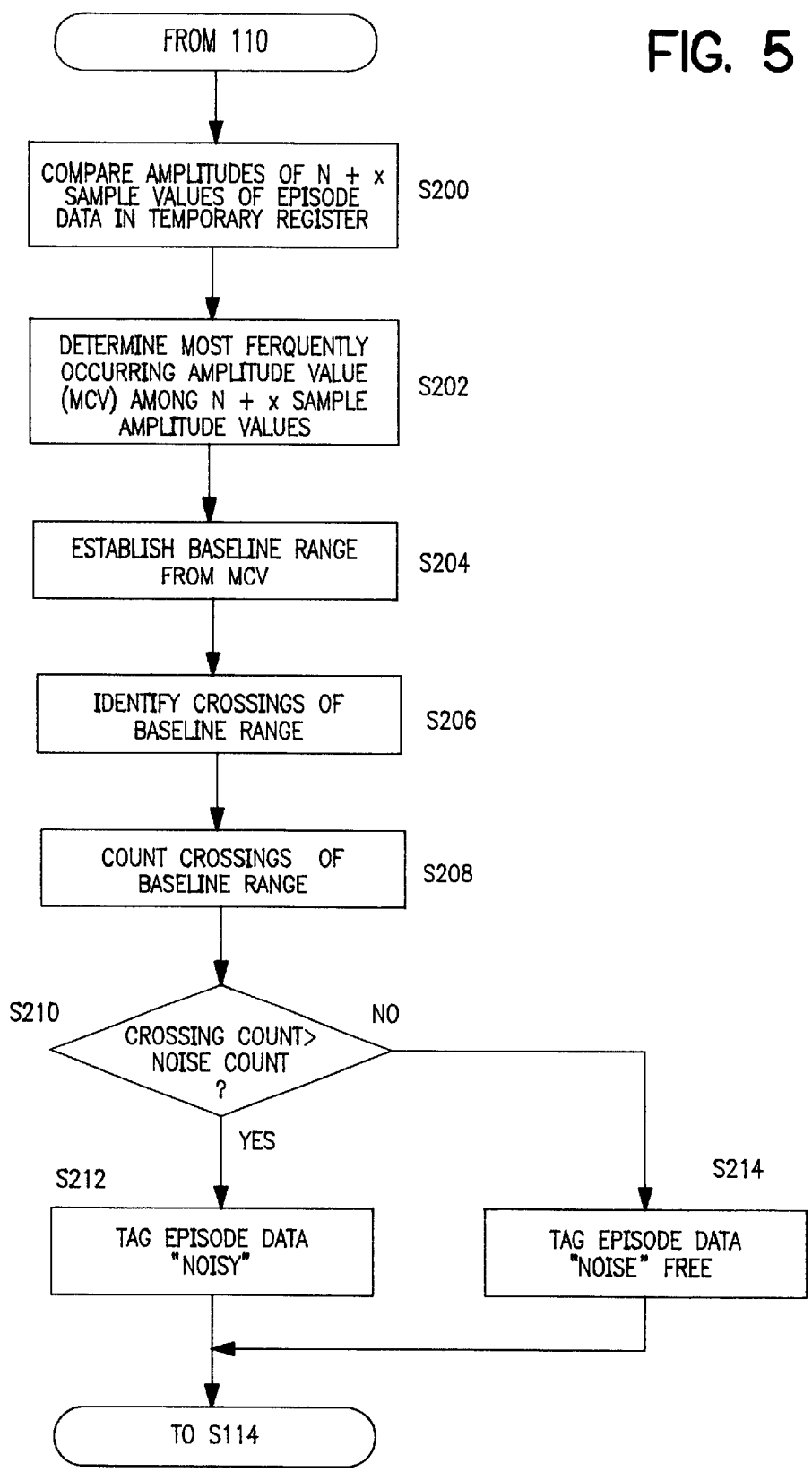

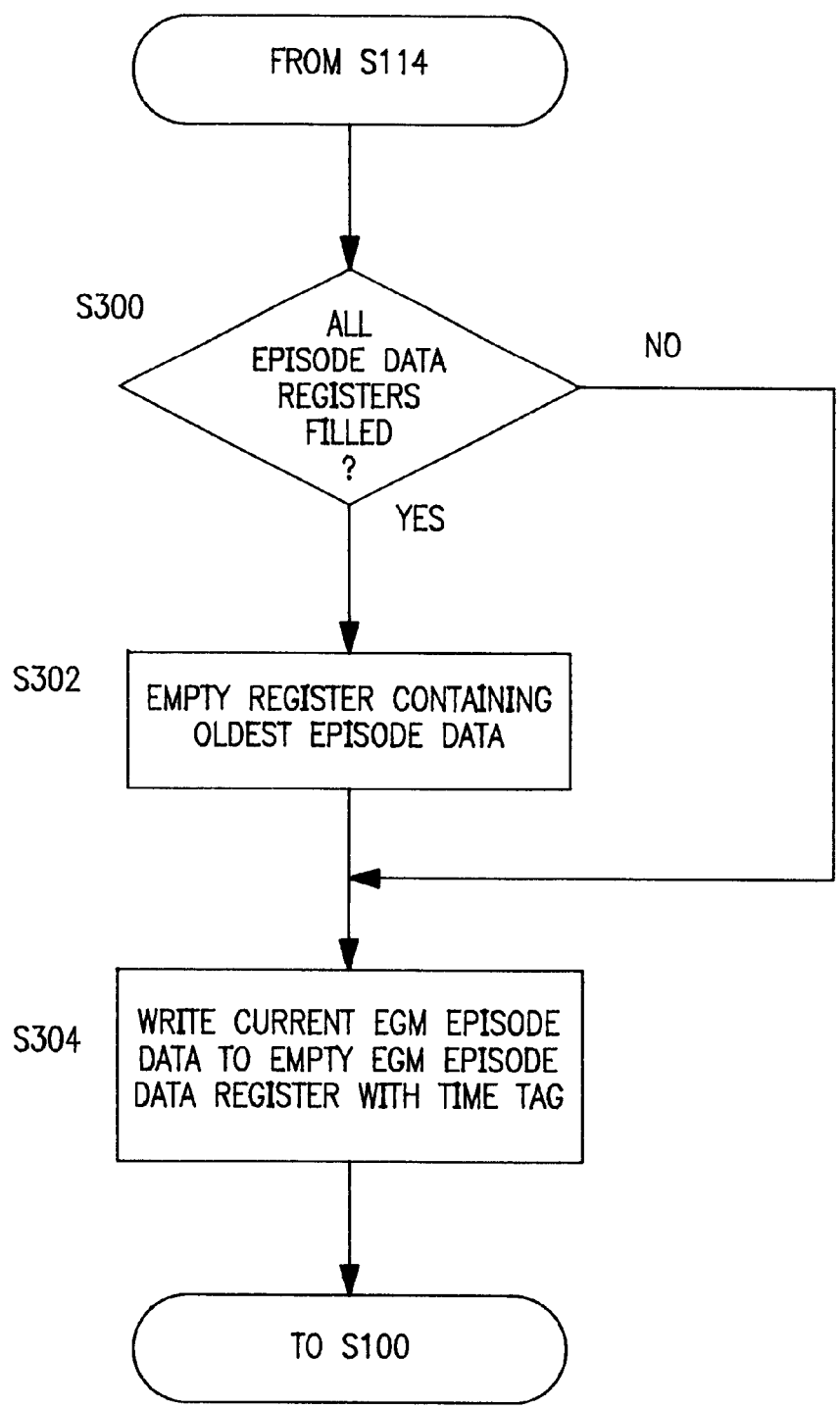

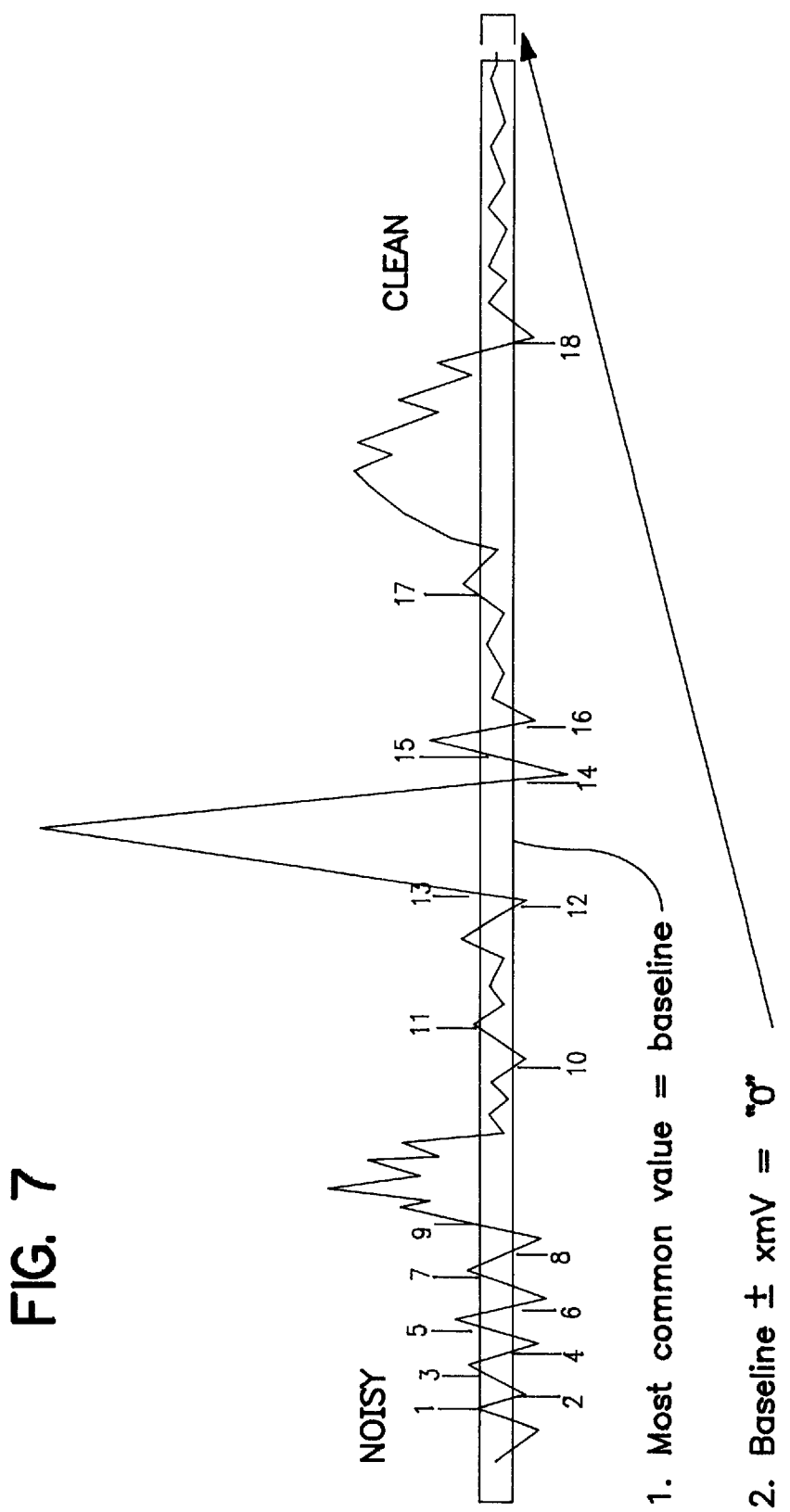

US 6,230,059 B1

IMPLANTABLE MONITOR

FIELD OF THE INVENTION

The present invention relates to discrimination of noisy physiologic data from relatively noise free physiologic data and selective storage thereof in an implantable medical device (IMD) and more particularly to methods and apparatus for discriminating noisy and relatively noise-free cardiac electrogram (EGM) episode data and selectively storing the noisy and noise-free EGM episode data in separate EGM data registers for later retrieval and analysis by a physician.

BACKGROUND OF THE INVENTION

There are many instances where it is desirable to be able to diagnose intermittent spontaneous cardiac arrhythmias in ambulatory patients. Frequently faintness, syncope, and tachyarrhythmia palpitation symptoms cannot be induced and observed by the physician in tests conducted in a clinic. For many years, such patients have been equipped with external ECG monitoring systems, e.g., the patient-worn, real time Holter monitors, that continuously sample the ECG from skin electrodes and record it over a certain time period. Then, the ECG data must be analyzed to locate evidence of an arrhythmia episode from which a diagnosis can be made.

As described in commonly assigned U.S. Pat. No. 5,312, 446 and in U.S. Pat. No. 4,947,858, both incorporated herein by reference, the externally worn ECG recorders have inherent limitations in the memory capacity for storing sampled ECG and EGM data. Cost, size, power consumption, and the sheer volume of data over time have limited real time external Holter monitors to recording 24 hour segments or recording shorter segments associated with arrhythmias that are felt by the patient who initiates storage.

The use of the externally worn Holter monitor coupled with skin electrodes is also inconvenient and uncomfortable to the patient. The skin electrodes can work loose over time and with movement by the patient, and the loose electrodes generates electrical noise that is recorded with the EGM signal and makes its subsequent analysis difficult. It has long been desired to provide an implantable monitor or recorder that is hardly noticeable by the patient and provides the capability of recording only EGM data correlated with an arrhythmia episode that is automatically detected.

Over the last 40 years, a great many IMDs have been clinically implanted in patients to treat cardiac arrhythmias and other disorders including implantable cardioverter/defibrillators (ICDs) and pacemakers having single or dual chamber pacing capabilities, cardiomyostimulators, ischemia treatment devices, and drug delivery devices. Recently developed implantable pacemakers and ICDs have been provided with sophisticated arrhythmia detection and discrimination systems based on heart rate, the morphology and other characteristics of the atrial and ventricular EGM and other characteristics of the EGM. Most of these IMDs employ electrical leads bearing bipolar electrode pairs located adjacent to or in a heart chamber for sensing a near field EGM or having one of the electrodes located on the IMD housing for sensing a far field, unipolar EGM. In either case, the near field or far field EGM signals across the electrode pairs are filtered and amplified in sense amplifiers coupled thereto and then processed for recording the sampled EGM or for deriving sense event signals from the EGM.

In current IMDs providing a therapy for treating a cardiac arrhythmia, the sense event signals and certain aspects of the sampled EGM waveform are utilized to automatically detect a cardiac arrhythmia and to control the delivery of an appropriate therapy in accordance with detection and therapy delivery operating algorithms. In such cardiac IMDs providing pacing or cardioversion/defibrillation therapies, both analog and digital signal processing of the EGM is continuously carried out to sense the P-wave and/or R-wave events and to determine when a cardiac arrhythmia episode occurs. For example, a digital signal processing algorithm is employed to distinguish various atrial and ventricular tachyarrhythmias from one another. When a tachyarrhythmia episode is detected, at least selected EGM signal segments and sense event histogram data or the like are stored on a FIFO basis in internal RAM for telemetry out to an external programmer at a later time. Many of these IMDs are also capable of being operated to sample the EGM and transmit real time EGM data of indefinite length via uplink telemetry transmissions to the external programmer when a real time telemetry session is initiated by the medical care provider using the programmer.

Implantable cardiac monitors have also been developed and clinically implanted that employ the capability of recording cardiac EGM data for subsequent interrogation and uplink telemetry transmission to an external programmer for analysis by a physician. The recorded data is periodically telemetered out to a programmer operated by the medical care provider in an uplink telemetry transmission during a telemetry session initiated by a downlink telemetry transmission and receipt of an interrogation command.

The MEDTRONIC® Reveal™ insertable loop recorder is a form of implantable monitor that is intended to be implanted subcutaneously and has a pair of sense electrodes spaced apart on the device housing that are used to pick up the cardiac far field EGM which in this case is also characterized as a "subcutaneous ECG". The Reveal™ insertable loop recorder samples and records one or more segment (depending on the programmed operating mode) of such far field EGM or subcutaneous ECG signals when the patient feels the effects of an arrhythmic episode and activates the recording function by applying a magnet over the site of implantation. For example, the storage of a programmable length segment of the EGM can be initiated when the patient feels faint due to a bradycardia or tachycardia or feels the palpitations that accompany certain tachycardias. The memory capacity is limited, and so the segments of such EGM episode data that are stored in memory can be written over with new EGM episode data when the patient triggers storage and the memory is full. The most recently stored segment or segments of episode data is transmitted via an uplink telemetry transmission to an external programmer when a memory interrogation telemetry session is initiated by the physician or medical care provider using the programmer. Aspects of the Reveal™ insertable loop recorder are disclosed in commonly assigned PCT publication WO98/02209.

More complex implantable monitors and pacemaker IPGs of this type but having more electrodes arranged in a planar array on the device housing are disclosed in commonly assigned U.S. Pat. No. 5,331,966, incorporated herein by reference. Three electrodes are employed to provide a pair of orthogonal sensed EGM or "subcutaneous ECG" signals at the subcutaneous implantation site. A lead can be employed in a disclosed pacemaker embodiment to locate a bipolar electrode pair in a heart chamber to provide an additional near field EGM sense signal from which the P-wave or R-wave can be sensed (depending on the location of the bipolar electrode pair) and through which pacing pulses can be applied to the atrium or ventricle. Recording of the near field and far field EGM episode data can be invoked automatically by detection of a bradycardia or satisfaction of tachyarrhythmia detection criteria or can be manually commenced by the patient using an external limited function programmer or can be commenced by the physician using a full function programmer.

In all of these IMDs having a cardiac monitoring function, the cardiac EGM is continually sensed and sampled in such monitors and recording of EGM episode data is triggered in a variety of ways. The relatively inexpensive and simple to implant Reveal™ insertable loop recorder has been favorably compared to the "black box" of an aircraft by physicians that have prescribed its implantation and use in a number of patients. Recordings of EGM episode data triggered by the patient using the relatively simple Reveal™ insertable loop recorder have proven to be of great value in diagnosing the causes of symptoms felt by the patients and in prescribing the implantation and programming of more complex therapy delivery IMDs, e.g., multi-programmable physiologic DDDR pacemakers and single and dual chamber ICDs.

However, many times patients are either unaware of "silent" cardiac arrhythmias or are asleep or fail to activate the recording function when they recover from syncope (i.e., have fainted) when bradycardias and tachyarrhythmias occur, and so the accompanying EGM episode data is not recorded. It is desired to be able to automatically detect an arrhythmia and to initiate recording of the EGM data without having to rely upon the patient as disclosed in the above-incorporated '966 patent. But, the subcutaneous location environment of the sense electrode pair or pairs on the device housing is relatively noisy due to electromyographic signals generated by adjacent muscle groups that are exercised by the patient. Limb and trunk movements or even breathing can generate noise spikes that are superimposed upon the far field EGM signal and can make it appear to reflect a higher heart rate than the actual heart rate. The electromyographic noise level is not as pronounced in relation to the EGM signal level when bipolar sense electrode pairs located in or close by the atrium and ventricle are employed as is typically the case with bipolar implantable pacemakers and ICDs. Consequently, it is usually possible to filter out such noise in the sense amplifiers of such IMDs. And, the patient implanted with the Reveal™ insertable loop recorder can be instructed to assume a quiet body state when he/she initiates recording. Moreover, even if noise artifacts are recorded, they are recorded within EGM episode data that does represent an arrhythmia felt by the patient.

In this context, if an implantable monitor of this type is implemented with an automatic arrhythmia detection function, it will automatically commence the recording of the EGM episode data when noise artifacts are superimposed on the EGM signal being monitored and if the detection algorithm mistakenly detects an arrhythmia as a consequence. On the other hand, sometimes such noise is present during an actual arrhythmia of interest that is correctly detected, triggering the recording of EGM episode data that is of interest but is also noisy. Due to the limited memory capacity, the EGM data episode that is corrupted by noise signals will be written over earlier recorded EGM episode data that is either also corrupted or is relatively noise free and either does or does not actually represent an arrhythmia episode of interest. The physician may find that the EGM episode data that is later uplink transmitted and displayed by the programmer is simply corrupted and of no value in diagnosing the patient's cardiac condition. Then, the physician may have to program the IMD detection algorithm differently (if it is possible to do so) or have to program the automatic detection and recording capability off and rely upon the patient to trigger the recording of EGM episode data when the onset of an arrhythmia is felt.

Thus, a need exists for a simple system for providing the automatic detection and recording functions in an implantable monitor of this type while avoiding filling the memory registers with EGM episode data that is noise corrupted.

SUMMARY OF THE INVENTION

It is therefore an object of the present invention to provide a simple system in an IMD for automatically discriminating noisy physiologic signals from relatively noise free physiologic signals and for storing them in separate memory registers to preserve such data for retrieval at a later time.

The present invention can be implemented in an implantable monitor having limited memory capacity that is allocated into at least two memory registers for storing noisy and noise free EGM episode data on a FIFO basis. Preferably, greater number of memory registers are provided that are allocated to provide a plurality of noisy EGM episode data registers to store a corresponding plurality of noisy EGM episode data sets on a FIFO basis and another plurality of noise free EGM episode data registers to store a corresponding plurality of relatively noise free EGM episode data sets on a FIFO basis.

The discrimination of noisy EGM data from relatively noise free EGM data is preferably accomplished in a simplified manner that does not require extensive analysis of the EGM and correspondingly complex and expensive hardware and software. In the context of monitoring and recording EGM episode data that will be subsequently viewed and analyzed by a physician, discrimination of noisy data from relatively noise free data with absolute certainty is not required at the time of recording. There is value to the physician in recording and being able to view and analyze both noisy and relatively noise free EGM episode data. The present invention advantageously provides storage of both noisy and relatively noise free EGM episode data and avoids recording only noisy EGM episode data in a relatively simple and inexpensive manner.

Preferably, the discrimination of noisy EGM episode data from relatively noise free EGM episode data commences when arrhythmia detection criteria are satisfied. The arrhythmia detection criteria can be relatively simple, e.g., simple rate detection, or can be more sophisticated and take other characteristics of the EGM data into account. The EGM data comprises sampled amplitude values, and the discrimination algorithm preferably determines that the EGM data is likely noisy when it includes a higher number of amplitude transitions with respect to a baseline than would be due to any bradycardia, normal sinus rhythm or tachyarrhythmia. Preferably, the most frequently occurring amplitude value in the data set is determined, and a baseline amplitude value or range is derived from the most frequently occurring amplitude value. Then, crossings of the baseline value are determined, and a crossing count of the total number of crossings of the baseline value is made. The crossing count is compared to a noise threshold count, and the EGM episode data is tagged as noisy if the crossing count exceeds or equals the noise threshold count or is tagged as noise free if the noise threshold count is less than the crossing count. The noise threshold count is preferably made programmable by the physician to account for variations in noise environments at the implantation site and along the sensing vector in individual patients. The baseline amplitude is also preferably a range to filter out and not recognize low amplitude variations from the most frequently occurring amplitude value.

It is further contemplated that the real time clock be incorporated within the operating system in order to provide a time tag with the stored EGM episode data to determined whether or not arrhythmia episodes are circadian.

The present invention advantageously improves the performance of relatively simple implantable monitors that have very limited signal filtration and memory capacity and that are implemented in digital logic circuitry. It provides that at least some relatively noise free EGM episode data can always be recorded and preserved if noise free conditions are present at least some of the time when an actual arrhythmia episode occurs and satisfies the detection criteria. The present invention can also be implemented in more complex and sophisticated, micro-processor based implantable monitors and therapy delivery IMDs.

While the present invention can be advantageously implemented in such IMDs of these types using one or more pair of subcutaneously disposed electrodes on the IMD housing or extended therefrom on leads, it can also be employed in reference to EGM signals derived from unipolar or bipolar electrode pairs having one or both electrodes disposed about or in one or more heart chamber.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein:

FIG. 4 is a flow chart illustrating the steps of carrying out the recording of EGM data in accordance with the present invention;

FIG. 5 is a flow chart illustrating the noise discrimination step S112 of FIG. 4 in greater detail;

FIG. 6 is a flow chart illustrating the data storage steps S116 and S118 of FIG. 4 in greater detail; and FIG. 7 illustrates noisy and relatively noise free portions of an EGM tracing and the steps of the combined flow charts of FIGS. 4–7.

DETAILED DESCRIPTION OF THE PREFERRED EMBODIMENTS OF THE INVENTION

Figure 1:
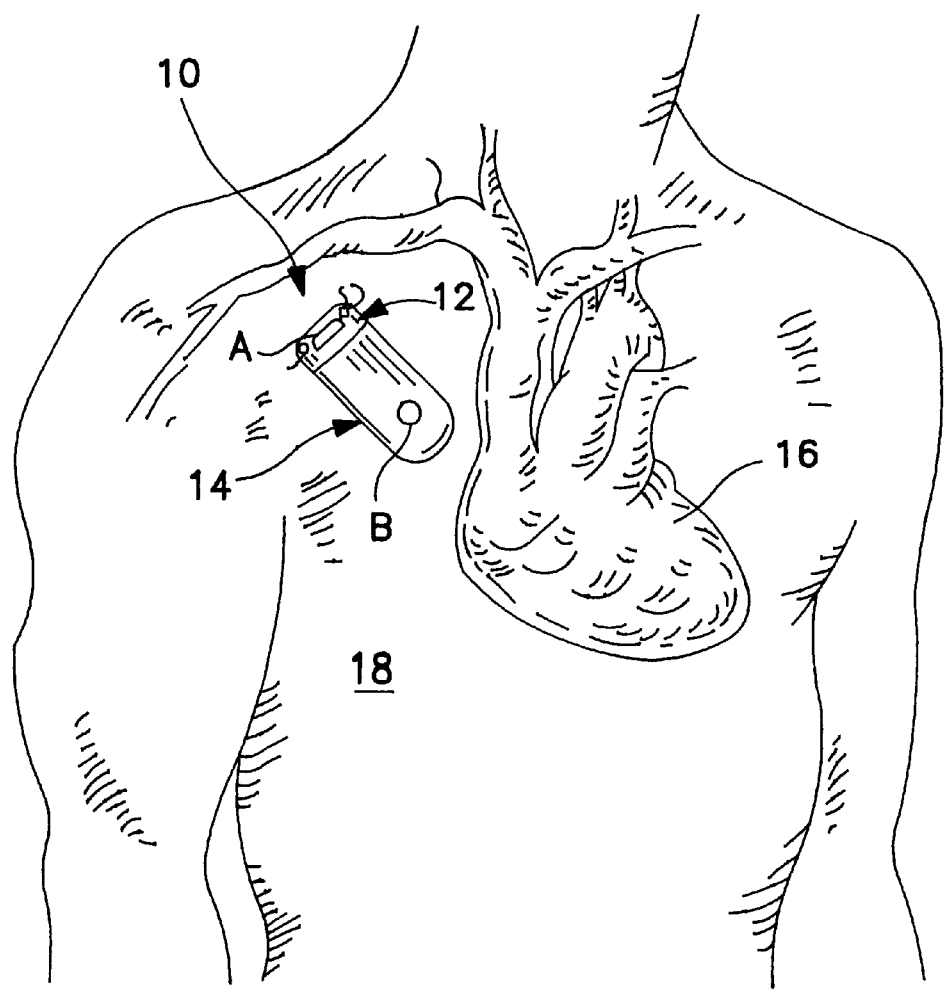
FIG. 1 is a view of one embodiment of an implantable cardiac monitor implanted subcutaneously in a patient's body having at least one pair of subcutaneous EGM electrodes on its housing for sensing a far field EGM signal in which the present invention is advantageously implemented.
Figure 2:
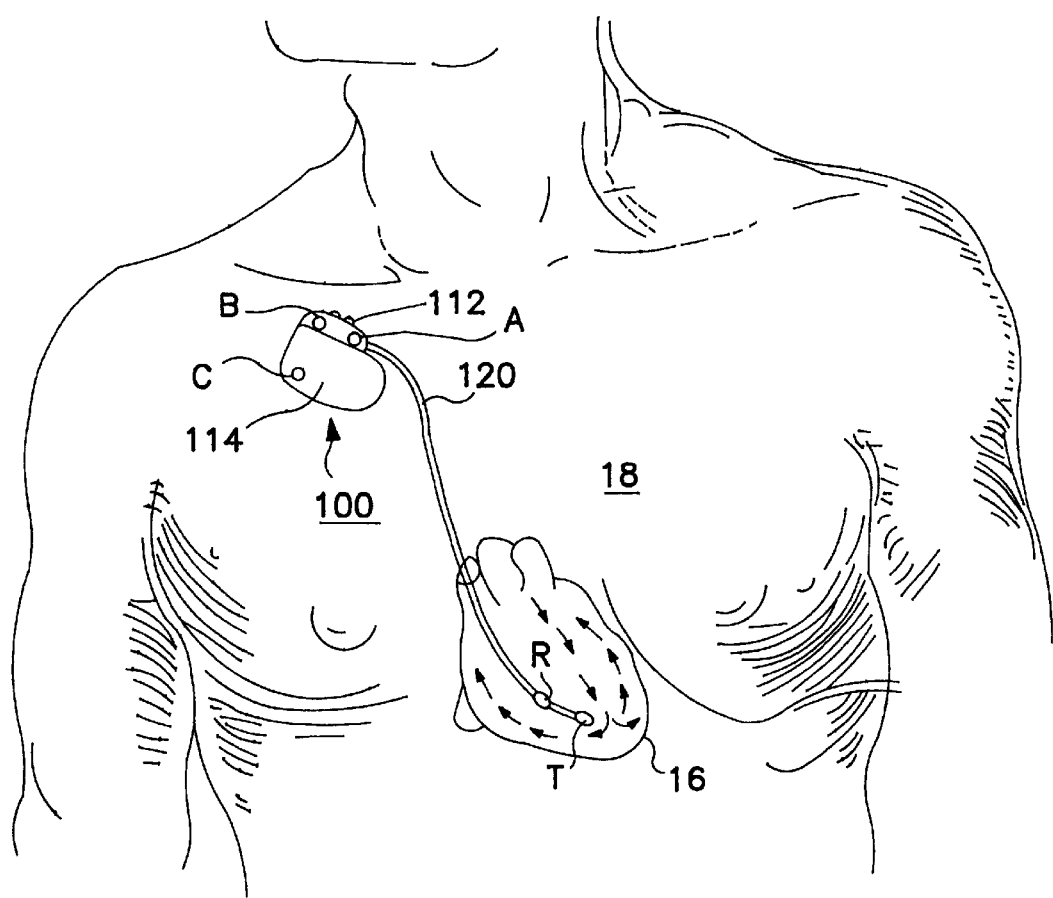
FIG. 2 is a view of another embodiment of an implantable cardiac monitor or cardiac monitor and therapy delivery device implanted subcutaneously in a patient's body having orthogonally disposed subcutaneous EGM electrodes on its housing for sensing at least two far field EGM signals in which the present invention is advantageously implemented.

The noise discrimination and data storage methods and apparatus of the present invention find particular utility in cardiac EGM monitors that have EGM sense electrodes locate where electromyographic noise can contaminate the EGM signal and corrupt it. Consequently, they will be described in conjunction with such monitors or therapy delivery IMDs as illustrated in FIGS. 1 and 2. However, it will be understood that the present invention is not so limited and that the noise discrimination and data storage methods and apparatus of the present invention can be used in other cardiac or other electrical signal monitors implanted in the body or coupled externally to the body.

FIG. 1 is a simplified schematic view of an implantable cardiac monitor 10 embodying the improvements of the present invention implanted subcutaneously in the upper thoracic region of the patient's body 18 and displaced from the patient's heart 16. The housing of the cardiac monitor 10 takes the shape of the MEDTRONIC® Reveal™ insertable loop recorder (shown enlarged in scale to the body 18) and comprises a non-conductive header module 12 attached to a hermetically sealed enclosure 14. The enclosure 14 contains the operating system of the cardiac monitor 10 and is preferably conductive but may covered in part by an electrically insulating coating. A first, subcutaneous, sense electrode A is formed on the surface of the header module 12 and a second, subcutaneous, sense electrode B is formed by an exposed portion of the enclosure 14. A feedthrough extends through the mating surfaces of the header module 12 and the enclosure 14 to electrically connect the first sense electrode A with the sensing circuitry within the enclosure 14, and the conductive housing electrode B is directly connected with the sensing circuitry. One form of coupling the header module 12 and enclosure 14 together is disclosed in commonly assigned U.S. Pat. No. 5,851,221, incorporated herein by reference.

The electrical signals attendant to the depolarization and re-polarization of the heart 16 are referred to as the cardiac EGM and are sensed across the sense electrodes A and B. The cardiac monitor 10 is sutured to subcutaneous tissue at a desired orientation of its electrodes A and B to the axis of the heart 16 to detect and record the EGM in a sensing vector A-B for subsequent uplink telemetry transmission to an external programmer (shown in FIG. 3). FIG. 1 shows only one such possible orientation of the sense electrodes A and B and sense vector A-B. Electromyographic signals are also generated in the muscles of the chest of the patient that can also be detected and recorded as described above at this subcutaneous location of the sense electrodes A and B. The relative magnitudes of the EGM signal and electromyographic signals can depend on their source and propagation direction with respect to the sense vector A-B In general, the hermetically sealed enclosure 14 includes a lithium battery, circuitry that controls device operations and records arrhythmic EGM episode data in memory registers, and a telemetry transceiver antenna and circuit that receives downlink telemetry commands from and transmits stored data in a telemetry uplink to the external programmer. The circuitry and memory may be implemented in discrete logic or a micro-computer based system with A/D conversion of sampled EGM amplitude values. One exemplary operating system that can be modified in accordance with the present invention is described in the above-incorporated '209 PCT application.

FIG. 2 is a simplified schematic view of a further IMD 100 that can function as a therapy delivery device and/or a cardiac monitor embodying the improvements of the present invention implanted subcutaneously in the upper thoracic region of the patient's body 18 and displaced from the patient's heart 16. This IMD 100 preferably takes the form of the IMDs that are disclosed in the above-incorporated '966 patent and comprises an endocardial lead 120 coupled at its proximal end to connector elements of a header module 112 and extending by a transvenous route into the right ventricle of the heart 16, in this illustrated case. The endocardial lead 120 takes the form of a bipolar lead of any of the well known types having a pair of closely spaced apart distal ring and tip electrodes R and T that can be used to sense the near field EGM in the ventricle and can be used to deliver pacing pulses to the ventricle.

The header module 112 is attached to a hermetically sealed enclosure 114 which contains the operating system of the IMD 100. Feedthroughs extend between the circuitry of the operating system, through the enclosure wall and into the header module 112 to make electrical connections with the lead 120 and to one or more sense electrode, e.g., the depicted sense electrodes A and B, formed on the surface of the header module 112. A third sense electrode C is formed by an exposed portion of the enclosure 114 and is directly connected with the sensing circuitry within the enclosure 114.

In this case, the sense electrodes A, B and C are arranged in a planar subcutaneous electrode array, and the cardiac monitor 10 is sutured to subcutaneous tissue at a desired orientation of its sense electrodes A, B, C to the axis of the heart 16. The sense electrodes A, B, C can be coupled in pairs to sense the far field EGM along three sense vectors A-B, B-C and A-C. Moreover, distal sense electrodes R and T define a further bipolar, near field sense vector that is axially aligned to the heart 16. One of the distal sense electrodes R or T can alternatively be paired with one of the subcutaneous electrodes A, B or C in a unipolar sensing mode to sense along a further, far field, ventricular EGM sensing vector. A variety of other sense electrode arrays and sense vectors are disclosed in the above-incorporated '966 patent, and the present invention can be employed to process EGM episode data derived from any pairing of these sense electrodes.

Figure 3:
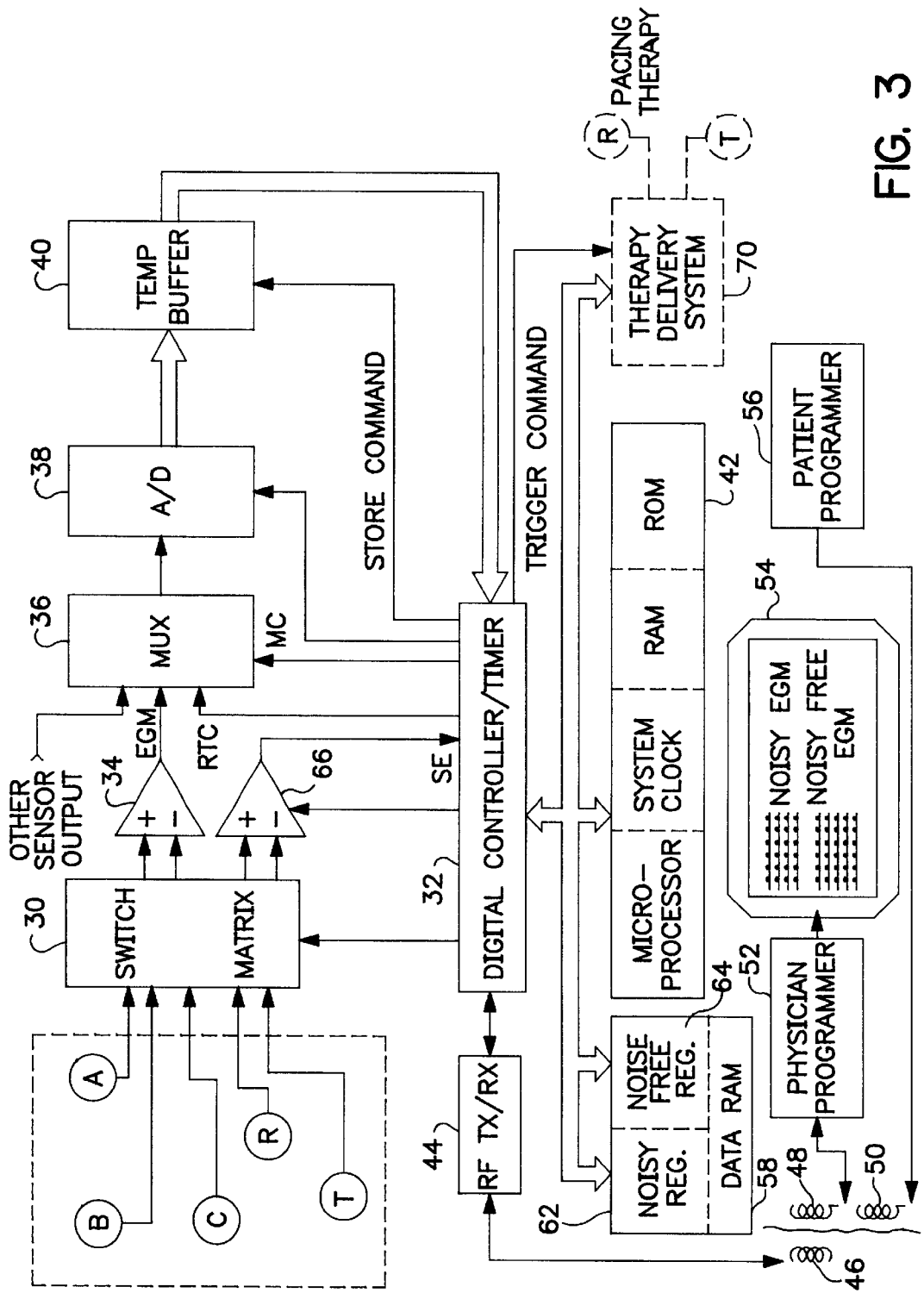
FIG. 3 is a schematic block diagram of major functional blocks of one embodiment of an operating system that can be employed in the IMD embodiments of FIGS. 1 and 2 to carry out the recording of EGM data in accordance with the present invention.

Again, electromyographic signals are also generated in the muscles of the chest of the patient that can also be detected and recorded as described above at this subcutaneous location of the sense electrode array and sometimes in particular locations of the sense electrodes R and T in the heart or unipolar pairing of such electrodes to a subcutaneous electrode. The relative magnitudes of the EGM signal and electromyographic signals can depend on their source and propagation direction with respect to the sense vector A-B A simplified IMD operating system 60 is depicted in FIG. 3 in conjunction with the attached lead 120 and subcutaneous electrodes A, B and C of IMD 100 and in relation to a physician operated, full function, programmer 52 and a patient operated, limited function programmer 56 and related programmer components. The operating system 60 is a modification of the operating systems disclosed in the above-incorporated '966 patent or '209 PCT publication for automatically initiating the storage of selected far field EGM episode data in a register of noisy data registers 62 or a register of noise free data registers 64 of data storage RAM 58 and optionally providing a therapy, e.g. a pacing therapy. It will be realized from the following discussion that selected portions of the IMD operating system 60 can be employed to perform more simplified monitoring functions with or without a therapy delivery function in variations of the implantable monitor 10.

The operations of the operating system 60 are controlled by the microcomputer 42 comprising a micro-processor, system clock, on-board RAM and ROM, operating by stored operating software routines, and a digital controller/timer circuit 32. EGM signal processing, EGM episode data storage, uplink and downlink telemetry, and optional therapy delivery functions are performed by further circuitry coupled with the digital controller/timer circuit 32. A data and control bus 72 and various control lines interconnect these components in a well known manner. Power to these components is supplied by a conventional implantable battery and power supply that are not shown to simplify the drawing.

The optional therapy delivery system 70 is preferably a programmable pacing output pulse generator coupled to the distal electrodes 14 and 16 for applying pacing pulses on demand and at a pacing rate dependent upon the physiologic requirements for cardiac output derived from analysis of an output signal of a physiologic or activity sensor in a manner well known in the art. The therapy delivery system can alternatively comprise a dual chamber pacemaker or ICD having appropriate sets of pacing and cardioversion/defibrillation electrodes arrayed about the heart chambers in various combinations that are well known in the art.

A transcutaneous RF telemetry system of a type well known in the art is employed in telemetry sessions initiated by the physician operating the programmer 52 including downlink and uplink telemetry transmissions of RF signals between the external antenna coil 48 and the implanted telemetry coil 46 and associated RF telemetry transmitter/receiver circuit 44 within the enclosure 14 or 114. A downlink telemetry transmission is initiated in order to effect programming of operating system operating modes or parameter values of the operating system 60 stored in the RAM and ROM in microcomputer 42 or to interrogate such programmed modes and values and to retrieve data stored in the registers of data storage RAM 58. All of the uplink telemetered data is displayed on the display 54 for analysis by the physician. The telemetry out of the EGM episode data, any other sensor data and the operating modes and parameter values is preferably implemented employing pulse position modulation techniques described in commonly assigned U.S. Pat. No. 5,127,404, incorporated herein by reference. Such high rate transmission techniques facilitate the telemetry out of time varying digitized EGM data.

A limited function external patient programmer 56 coupled with a further antenna coil 50 can also be provided to the patient to be used by the patient to trigger storage of EGM data when the patient feels the onset of a bradycardia or tachycardia episode. In a simplified system, it is contemplated that the patient programmer 56 and antenna 50 may be eliminated in favor of a magnetically actuable reed switch implanted in the device and coupled to the digital controller/timer circuit 32 that may be closed by the patient placing a magnet over the IMD 10, 100 as is well known in the prior art.

The subcutaneous sense electrodes A, B and C, are coupled to the switch matrix 30 which operates under the control of the digital controller/timer circuit 32 to switch the far field EGM signal developed across at least one electrode pair A-B, B-C or C-B at a time through amplifier 34 to one input of multi-plexer 36. The distal ring and tip sense or pace/sense electrodes R and T of lead 120 are also optionally coupled to the switch matrix 30 and selected in a similar manner to apply a near field EGM or far field EGM to the input of the multiplexer 36 depending upon how the electrodes are paired.

A selected electrode pair is also coupled by the switch matrix 30 under the control of the digital controller/timer circuit 32 to the input terminals of a further sense amplifier 66 of a type well known in the art for comparing an input signal amplitude to a programmable sensing threshold value. The sense amplifier 66 is triggered by a high amplitude feature of the EGM characteristic of the R-wave and exceeding the sensing threshold value to provide a sensed event (SE) signal to the digital controller/timer circuit 32 for timing and control purposes. Sensed event marker signals can also be developed and supplied to the multi-plexer 36 to provide marker channel (MC) symbols that can be stored with EGM episode data that is placed in permanent storage.

Moreover, the heart rate is determined from the intervals between successive sensed events generated by sense amplifier 66, and the heart rate is compared to a programmed bradycardia detection heart rate and/or a programmed tachycardia heart rate to trigger storage of EGM episode data derived from the selected sense electrode pairs. In addition, as noted below, N successive EGM sample values can also be examined against additional arrhythmia detection criteria.

Multi-plexer 36 also operates under commands delivered by digital controller/timer circuit 32 to direct the EGM signal or a sensor output signal or a real time clock (RTC) time tag to A/D converter 38. A/D converter 38 samples the time varying analog EGM signal and digitizes the sampled values in a well known fashion. The digitized sample values of the EGM output by the A/D converter 38 are applied to a temporary buffer 40 which shifts the digital data through its stages in a FIFO manner under the control of the digital controller/timer circuit 32. The temporary buffer 40 may have a capacity of 20 to 30 seconds of continuous digitized EGM data although longer periods are contemplated in certain situations described in the above-incorporated '966 patent.

For purposes of the following discussion, temporary buffer 40 is characterized as having N+x stages for temporarily storing N sample values of EGM episode data prior to an arrhythmia detection or patient generated command to store data (pre-detection data) and for temporarily storing x sample values thereafter (post detection data). The number N can be relatively short or long in comparison to the number x to provide for storage of the EGM data of the episode following onset of the arrhythmia. In any case, both N and x are preferably made programmable to allow the physician to determine what lengths of pre-detection and post detection episode data is best to record for the particular patient.

The EGM sample values are continually generated by A/D converter 38 and shifted serially through the N+x stages in a FIFO order, and permanent data storage is not initiated unless a STORE signal is generated. In accordance with the present invention, when a STORE command is generated, a parallel transfer of the N+x sample values is effected into a scratchpad RAM register of microcomputer 42 via data bus 72 for noise analysis and discrimination. Then, the N+x sample values are then stored with the associated real time clock (RTC) time tag and event markers on a FIFO basis either in the noisy EGM data register among the plurality of noisy data registers 62 or in a noise free EGM data register among the plurality of noise free data registers 64. The STORE command is generated when a particular arrhythmia detection criteria is satisfied or when a storage command from the patient programmer 56 or a like command from the physician programmer 52 is received through the radio frequency transmitter/receiver circuit block 44 or the patient applies a magnet to close a reed switch as described above.

The simplest arrhythmia detection process involves comparison of sensed event rate to a programmed bradycardia rate for detection of bradycardia or a programmed tachycardia rate for detection of a tachycardia. The N successive sample values accumulated in the temporary buffer 40 may therefore comprise several seconds over which heart rate is determined. The detection criteria may also involve examination of the N successive sample values against more sophisticated programmed tachyarrhythmia detection criteria as they are generated and enter the temporary buffer 40. In this case, the sample values shifted into the N initial stages of the temporary buffer 40 are examined continuously. When the arrhythmia detection criteria are satisfied, the N sample values preceding the satisfaction are shifted through the temporary buffer stages until a subsequent x sample values fill the buffer stages. The STORE command is then generated to effect the transfer or move of the block of data to a designated scratchpad register in RAM of the microcomputer 42.

In the context of an arrhythmia control device, such as an ICD, the number N may be relatively large, and the STORE command may precipitate storage of many seconds of EGM episode data preceding detection of a tachyarrhythmia followed by the continuation of the EGM episode data following detection and delivery of a therapy. In the context of a drug administration device, the STORE command may precipitate the storage of data related to the detection of an arrhythmia or an abnormal cardiac function detected by another sensor and the delivery of a bolus of medication.

In a certain segment of patients suffering recurring bouts of syncopy, the operating system of FIG. 3 (simplified by substitution of digital logic for the microprocessor within block 42) could be implanted with or without rate detection circuitry for detecting syncopy and automatically triggering the storage of data. Alternatively, it is contemplated that the limited function patient programmer 56 and transmitting antenna 50 be provided for use by the patient upon recovery from a bout of syncopy. When a patient experiences syncopy lasting more than a few seconds, they typically faint and recover a short time thereafter. The storage of several minutes of EGM prior to and during the syncoptal episode and for a time thereafter would constitute valuable data in the analysis of the rhythm disturbance precipitating the episode. When the patient commands data storage, the STORE command is delivered to the temporary buffer 40 after a delay to allow the storage of N sample values prior to and x sample values following the receipt of the patient command.

Further details pertaining to the operating system of FIG. 3 along with a description of other storage precipitating events that could be employed in the practice of the present invention are disclosed the above-incorporated '966 patent or '209 PCT publication. Moreover, reference is made to commonly assigned U.S. Pat. No. 5,782,876 for a comprehensive description of a wide variety of methods of detecting and discriminating various types of tachyarrhythmias from one another that have been used in IMDs or proposed for such use over the years, as well as a comprehensive new method, that could be employed in the practice of the present invention.

It will be understood that the operating system of FIG. 3 can be simplified to function with the relatively simple implantable monitor depicted in FIG. 1 or any other such system using only a pair of electrodes by at least eliminating the switch matrix 30 and multiplexer 36. The sensed event signal SE and the EGM signal can be developed from the single electrode pair. If noise levels are so high in such a system that they are detected by the sense amplifier 66, their frequency of occurrence will be erroneously interpreted as a tachycardia, triggering storage of the EGM episode data in the noisy registers 62. The physician can determine from observation that the EGM episode data simply represents noise and take appropriate action, e.g., reducing the sensitivity of the sense amplifier 66.

Attention is now directed to the flow charts of FIGS. 4–6 and the waveform diagram of FIG. 7 where the operating method and apparatus of the present invention are further depicted. In FIG. 5, the EGM is continually sampled and digitized in A/D converter 38 in step S100, and sample values are stored in the stages of the temporary buffer 40 in step S102. In step S104, the programmed arrhythmia detection criteria are continually applied to the N sample values and/or to the heart rate determined from the intervals between a set number of sensed event signals which correspond to the accumulation of N sample values.

In step S110, the EGM episode data is moved from the temporary buffer 40 to the temporary RAM register in microcomputer 42 when either an arrhythmia episode is detected in step S106 or a downlink telemetry storage command is received in step S108. The data block move initiated by the STORE command is delayed until the temporary buffer 40 is filled with x further EGM sample values following the N sample values.

In step S112, shown in greater detail in FIG. 5, the episode data sample values are analyzed with respect to the noise detection criteria to determine if the episode data is noisy or relatively free of noise. If the episode data is tagged "noisy" in step S112, it is moved into one of the noisy data registers 62 of data RAM 58 in step S116. Conversely, if the episode data is tagged "noise free" in step S112, it is moved into one of the noise free data registers 64 of data RAM 58 in step S118.

Any form of noise detection and discrimination of relatively noisy and noise free EGM episode data can be employed in step S112. While it is contemplated that all of the sampled N+x EGM sample values will be employed in step S112 to identify noisy or noise free EGM episode data, it will be understood that fewer than all of the N+x EGM sample values may be examined to determine if the EGM episode data is noisy.

FIG. 5 depicts one preferred form of the noise detection step S112 in greater detail. The amplitudes of all of the N+x sample values in the temporary data register in RAM in microcomputer 42 are compared in step S200, and a determination of the most frequently occurring amplitude value, i.e., the most common value (MCV), is made in step S202. A baseline is established from the MCV in step S204, and it is preferably defined as a range to filter out and not recognize low amplitude variations from the most frequently occurring amplitude value.

FIG. 7 illustrates an EGM tracing reconstituted from a set of EGM data values wherein noisy and relatively noise free or "clean" portions are shown. The most common value of the EGM sample values is likely to closely follow the isoelectric baseline between successive PQRST complexes associated with depolarizations of the atria and ventricles. The baseline in this illustration is defined as a +/– range from the derived MCV and it masks minor variations in the sample values when the sample values are not corrupted with noise. However, the noisy portions exceed or fall below the range that may be programmable by the physician using the programmer 52. The discrimination algorithm thus determines that the EGM data is likely to be contaminated with noise when it includes a higher number of amplitude transitions with respect to the baseline than would be due to any bradycardia, normal sinus rhythm or tachyarrhythmia.

Returning to FIG. 5, the crossings of the baseline range are identified in step S206 and are counted in step S208. The crossing count accumulated in step S208 is compared to a noise threshold count in step S210. The EGM episode data is tagged as noisy in step S212 if the crossing count exceeds or equals the noise threshold count or is tagged as noise free in step S214 if the noise threshold count is less than the crossing count. The noise threshold count is preferably made programmable by the physician to account for variations in noise environment at the implantation site and along the sensing vector in individual patients.

FIG. 6 depicts the FIFO storage of the EGM episode data in one of the noisy registers 62 in accordance with step S116 or in one of the noise free registers 64 of data RAM 58 in accordance with step S118. The EGM episode data within these registers is noted by date and time of recording (the time tag). If all data registers are filled as determined in step S300, then the register containing the oldest EGM episode data is emptied in step S302. The current EGM episode data is written into that empty register with its time tag in step S304. Alternatively, the register containing the oldest EGM episode data is identified step S302, and the current EGM episode data is simply written over the oldest EGM episode data in step S304.

The external physician programmer 52 may be employed by the physician in working up the patient in the course of a drug or electrophysiologic study. In such circumstances, the programmer software may be designed to instruct the digital controller/timer circuit 32 and the microprocessor within microcomputer circuit 42 to direct the output of the A/D converter 38 directly to the RF transmitter/receiver block 44 in real time for telemetry out, reception by the programmer 52 and display on the display panel 54. Alternatively, the physician programmer 52 may be employed to read out the contents of the noisy and noise free registers of data RAM 58 devoted to the storage of the digitized EGM episode data, other sensor derived data, and the time tag data for display and recording.

Returning to FIG. 3, the noisy and the noise free EGM episode data tracings are printed or displayed on display 54. The tracings may show that the noise artifacts of the noisy episode data caused it to be interpreted as a tachyarrhythmia by the tachyarrhythmia detection algorithm, during an underlying normal sinus rhythm or during a bradycardia or even during an actual tachycardia episode of another type, but also of interest. The noise free episode tracings should represent true arrhythmia episodes, and their recording is preserved advantageously in accordance with the invention.

The allocation of the number of noisy data registers 62 vs. noise free data registers 64 within data RAM can be programmed by the physician using the programmer 52 to maximize the accumulation of useful data of each type depending on the noise environment of a given patient. The data registers 62 and 64 are identified by addresses that also specifiy the length of each data register. Interrogatable time tag logs can also be maintained in data RAM 58 listing the times and dates of all of the noisy and relatively noise free arrhythmia episodes that were detected, stored and written over since the preceding interrogation to assist in diagnosing the patient's condition and reprogramming of the detection criteria, the noise discrimination criteria, and the allocation of data registers 62 and 64.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. In an implantable medical device adapted to be implanted in a patient and operated to record electrical signals of the body for later retrieval and review to aid in diagnosing a condition of the patient, a method for recording such data that may be corrupted by ambient electrical noise comprising the steps of:

sampling the electrical signals of interest and providing sample values;

commanding the storage of a sequence of sample values in a storage register from which the sample values can be retrieved for review at a later time; and in response to the commanded storage, examining the sequence of sample values to determine if the sequence of sample values is corrupted with noise or is relatively noise free; and if the sequence of sample values is determined to be corrupted by noise, storing the sequence of sample values in a storage register designated as a noisy storage register to only receive a sequence of sample values determined to be corrupted by noise; or if the sequence of sample values is determined to be relatively noise free, storing the sequence of sample values in a storage register designated as a relatively noise free storage register to only receive sample values determined to be relatively noise free.

2. The method of claim 1, wherein the number of noisy and relatively noise free storage registers of the implantable medical device are limited, and wherein said storing steps further comprise the steps of:

storing the sequence of sample values determined to be corrupted by noise in a noisy storage register on a FIFO basis, whereby the oldest sequence of sample values corrupted by noise is deleted if the noisy storage registers are already filled; and storing the sequence of sample values determined to be relatively free of noise in a noise free storage register on a FIFO basis, whereby the oldest sequence of sample values determined to be relatively free of noise is deleted if the noise free storage registers are already filled.

3. The method of claim 2, wherein the commanding step further comprises the step of:

receiving a storage command originating externally to the patient's body and commanding the storage of the sequence of sample values in a storage register.

4. The method of claim 2, wherein the commanding step further comprises the steps of:

monitoring a state of the electrical signals of interest with respect to detection criteria of a medical condition of interest; and commanding the storage of the sequence of sample values in a storage register when the electrical signals of interest satisfy the detection criteria.

5. The method of claim 1, wherein the commanding step further comprises the steps of:

monitoring a state of the electrical signals of interest with respect to detection criteria of a medical condition of interest; and commanding the storage of the sequence of sample values in a storage register when the electrical signals of interest satisfy the detection criteria.

6. The method of claim 1, wherein the commanding step further comprises the steps of:

receiving a storage command originating externally to the patient's body and commanding the storage of the sequence of sample values in a storage register.

7. The method of claim 1, wherein the electrical signals of the body comprise the cardiac EGM, the sample values are EGM sample values, and the sequence of EGM sample values comprise EGM episode data, and wherein the commanding step further comprises the step of:

receiving a patient initiated storage command originating externally to the patient's body and commanding the storage of EGM episode data in a storage register.

8. The method of claim 1, wherein the electrical signals of the body comprise the cardiac EGM, the sample values are EGM sample values, and the sequence of EGM sample values comprise EGM episode data, and wherein the commanding step further comprises the steps of:

comparing the EGM sample values to arrhythmia detection criteria of one or more tachyarrhythmia condition of interest; and commanding the storage of the EGM episode data in a storage register when a sequence of the EGM sample values satisfy the detection criteria.

9. In an implantable medical device adapted to be implanted in a patient and operated to record electrical signals of interest of the body for later retrieval and review to aid in diagnosing a condition of the patient, apparatus for recording sequences of such electrical signals that may be corrupted by ambient electrical noise comprising:

means for sampling the electrical signals of interest and providing sample values;

a data memory comprising at least one noisy storage register designated to only store a sequence of sample values determined to be corrupted by noise and at least one noise free storage register designated to only store a sequence of sample values determined to be relatively noise free;

means for commanding the storage of the sequence of sample values in a storage register of said data memory;

means for examining the sequence of sample values to determine if the sequence of sample values is corrupted with noise or is relatively noise free, and storing means operable, if the sequence of sample values is determined to be corrupted by noise, for storing the sequence of sample values in a noisy storage register and operable, if the sequence of sample values is determined to be relatively noise free, for storing the sequence of sample values in a noise free storage register.

10. The apparatus of claim 9, wherein:

said data memory comprises a plurality of noisy and relatively noise free storage registers; and said storing means further comprises means for storing the sequence of sample values in a noisy or noise free storage register on a FIFO basis, whereby the oldest sequence of sample values stored in the noisy or noise free storage register, respectively, is deleted.

11. The apparatus of claim 10, wherein the commanding means further comprises:

means for receiving a storage command originating externally to the patient's body and for commanding storage of the sequence of sample values in a storage register.

12. The apparatus of claim 10, wherein the commanding means further comprises:

means for monitoring a state of the electrical signals of interest with respect to detection criteria of a medical condition of interest; and means for commanding the storage of the sequence of sample values in a storage register when the electrical signals of interest satisfy the detection criteria.

13. The apparatus of claim 9, wherein the commanding means further comprises:

means for receiving a storage command originating externally to the patient's body and for commanding storage of the sequence of sample values in said temporary storage register.

14. The apparatus of claim 9, wherein the commanding means further comprises:

means for monitoring a state of the electrical signals of interest with respect to detection criteria of a medical condition of interest; and means for commanding the storage of the sequence of sample values in a storage register when the electrical signals of interest satisfy the detection criteria.

15. The apparatus of claim 9, wherein the electrical signals of the body comprise the cardiac EGM, the sample values are EGM sample values, and the sequence of EGM sample values comprise EGM episode data, and the commanding means further comprises:

means for receiving a storage command originating externally to the patient's body and for commanding storage of the EGM episode data in a storage register.

16. The apparatus of claim 9, wherein the electrical signals of the body comprise the cardiac EGM, the sample values are EGM sample values, and the sequence of EGM sample values comprise EGM episode data, and the commanding means further comprises:

means for comparing the EGM sample values to arrhythmia detection criteria of one or more tachyarrhythmia condition of interest; and means for commanding the storage of the EGM episode data in a storage register when a sequence of the EGM sample values satisfy the detection criteria.

17. In an implantable medical device adapted to be implanted in a patient and operated to record EGM episode data of the heart for later retrieval and review to aid in diagnosing a cardiac arrhythmia condition of the patient, a method for recording such EGM episode data that may be corrupted by ambient electrical noise comprising the steps of:

continuously sampling the cardiac EGM and providing a sequence of EGM sample values;

determining if the sequence of EGM sample values is corrupted with noise or is relatively noise free and designating the sequence of EGM sample values as noisy EGM episode data or noise free EGM episode data in response to the determination;

storing the noisy EGM episode data in a noisy storage register designated to only receive EGM sample values determined to be corrupted by noise; and storing the noise free EGM episode data in a noise free storage register designated to only receive sample EGM values determined to be relatively noise free.

18. The method of claim 17, wherein the number of noisy and relatively noise free storage registers of the implantable medical device are limited, and wherein said storing steps further comprise:

storing the noisy EGM episode data in a designated noisy storage register on a FIFO basis, whereby the oldest sequence of noisy EGM episode data is deleted if the noisy storage registers are already filled with noisy EGM episode data; and storing the noise free EGM episode data in a designated noise free storage register on a FIFO basis, whereby the oldest sequence of noise free EGM episode data is deleted if the noise free storage registers are already filled with noise free EGM episode data.

19. The method of claim 18, further comprising the steps of:

comparing a sequence of the EGM sample values to arrhythmia detection criteria of one or more tachyarrhythmia condition of interest; and commanding the storage of the EGM episode data in a storage register when a sequence of the EGM sample values satisfy the detection criteria.

20. The method of claim 18, further comprising the step of:

receiving a patient initiated storage command originating externally to the patient's body and commanding the storage of the EGM episode data in a storage register.

21. In an implantable medical device adapted to be implanted in a patient and operated to record EGM episode data of the heart for later retrieval and review to aid in diagnosing a cardiac arrhythmia condition of the patient, apparatus for recording such EGM episode data that may be corrupted by ambient electrical noise comprising:

means for continuously sampling the cardiac EGM and providing EGM sample values;

a data memory comprising at least one noisy storage register designated to only receive EGM sample values determined to be corrupted by noise and at least one noise free storage register designated to only receive EGM sample values determined to be relatively noise free;

means for temporarily storing a sequence of the EGM sample values;

means for determining if the temporarily stored sequence of EGM sample values is corrupted with noise or is relatively noise free and designating the sequence of EGM sample values as noisy EGM episode data or noise free EGM episode data, respectively, in response to the determination;

means for storing the noisy EGM episode data in a noisy storage register; and means for storing the noise free EGM episode data in a noise free storage register.

22. The apparatus of claim 21, wherein:

said data memory comprises a plurality of noisy and relatively noise free storage registers, and said storing means further comprise:

means for storing the noisy EGM episode data in a designated noisy storage register on a FIFO basis, whereby the oldest sequence of noisy EGM episode data is deleted if the noisy storage registers are already filled with noisy EGM episode data; and means for storing the noise free EGM episode data in a designated noise free storage register on a FIFO basis, whereby the oldest sequence of noise free EGM episode data is deleted if the noise free storage registers are already filled with noise free EGM episode data.

23. The apparatus of claim 22, further comprising:

means for comparing the temporarily stored sequence of EGM sample values to arrhythmia detection criteria of one or more tachyarrhythmia condition of interest; and means responsive to the comparing means for commanding the storage of the temporarily stored sequence of EGM sample values by said storing means in a determined one of said noisy or noise free storage registers when a sequence of the EGM sample values satisfy the detection criteria.

24. The apparatus of claim 22, further comprising:

means responsive to a patient initiated storage command originating externally to the patient's body for commanding the storage of the temporarily stored EGM sample values by said storing means in a determined one of said noisy or noise free storage registers.

25. The apparatus of claim 21, further comprising:

means for comparing the temporarily stored sequence of EGM sample values to arrhythmia detection criteria of one or more tachyarrhythmia condition of interest; and means responsive to the comparing means for commanding the storage of the temporarily stored sequence of EGM sample values by said storing means in a determined one of said noisy or noise free storage registers when a sequence of the EGM sample values satisfy the detection criteria.

26. The apparatus of claim 21, further comprising:

means responsive to a patient initiated storage command originating externally to the patient's body for commanding the storage of the temporarily stored EGM sample values by said storing means in a determined one of said noisy or noise free storage registers.

\* \* \* \* \*